(12) United States Patent
Hess et al.

(10) Patent No.: US 9,964,496 B2
(45) Date of Patent: May 8, 2018

(54) METHOD FOR THE QUALITY ASSESSMENT OF A COMPONENT PRODUCED BY MEANS OF AN ADDITIVE MANUFACTURING METHOD

(71) Applicant: MTU Aero Engines AG, Munich (DE)

(72) Inventors: Thomas Hess, Munich (DE); Alexander Ladewig, Bad Wiessee (DE)

(73) Assignee: MTU Aero Engines AG, Munich (DE)

( * ) Notice: Subject to any disclaimer, the term of this patent is extended or adjusted under 35 U.S.C. 154(b) by 290 days.

(21) Appl. No.: 14/827,346

(22) Filed: Aug. 17, 2015

(65) Prior Publication Data
US 2016/0054231 A1    Feb. 25, 2016

(30) Foreign Application Priority Data
Aug. 21, 2014    (DE) .................. 10 2014 216 567

(51) Int. Cl.
*G01N 37/00*    (2006.01)
*G01N 21/88*    (2006.01)
*G05B 19/418*    (2006.01)

(52) U.S. Cl.
CPC ... *G01N 21/8806* (2013.01); *G05B 19/41875* (2013.01); *G01N 2201/12* (2013.01); *G05B 2219/32191* (2013.01); *G05B 2219/32201* (2013.01); *G05B 2219/32212* (2013.01); *G05B 2219/32213* (2013.01); *Y02P 90/22* (2015.11)

(58) Field of Classification Search
CPC .......... G01N 21/8806; G05B 19/41875; Y02P 90/22
USPC ........................................................ 702/82
See application file for complete search history.

(56) References Cited

U.S. PATENT DOCUMENTS

2014/0009604 A1\* 1/2014 Hinderling ........... G01C 15/002
                                                                       348/142
2015/0254376 A1\* 9/2015 Pettersson ........... G06F 17/5004
                                                                       703/1

FOREIGN PATENT DOCUMENTS

| DE | 10 2004 017 769 B4 | 12/2004 |
| DE | 102004063388 A1 | 7/2006 |
| DE | 10 2011 009 624 A1 | 8/2012 |
| DE | 102011113445 A1 | 3/2013 |
| WO | 2012019577 A2 | 2/2012 |

OTHER PUBLICATIONS

Turner, I. Y., Thompson, D. C., Wood, K. L., Crawford, R. H., "Characterization of Surface Fault Patterns with Application to a Layered Manufacturing Process", Journal of Manufacturing Systems, Society of Manufacturing Engineers, Dearborn, MI, vol. 17, No. 1, Jan. 1998.

\* cited by examiner

*Primary Examiner* — Anthony Ho
(74) *Attorney, Agent, or Firm* — Barlow, Josephs & Holmes, Ltd.

(57) ABSTRACT

The invention relates to a method for the quality assessment of a component produced by means of an additive manufacturing method. In the course of the method, it is checked first of all whether the component violates predetermined absolute limits in order to rule out the existence of serious malfunctions in the additive manufacturing process. Subsequently, a component-dependent targeting process is determined. On the basis of this targeting process, the limits for deviations are established and deviating actual values of the component are isolated and assessed by means of various parameters.

8 Claims, 2 Drawing Sheets

Figure 1:
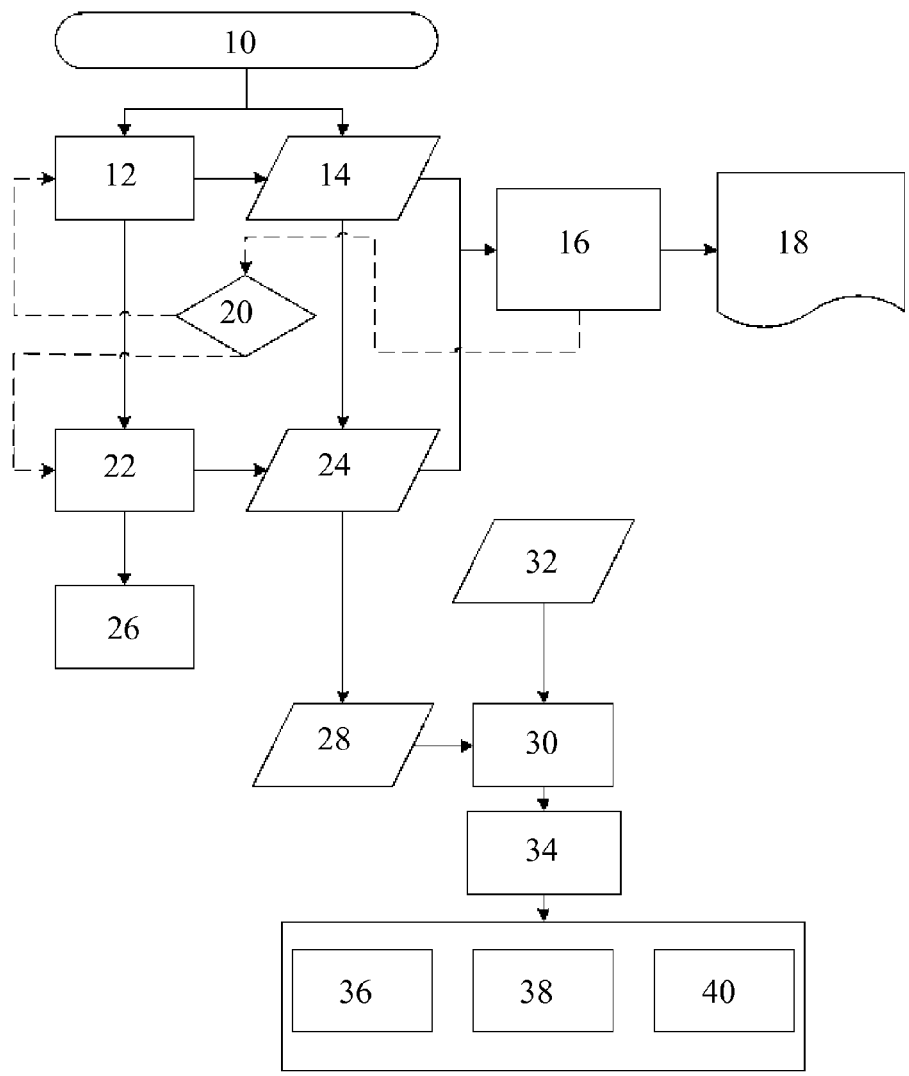

METHOD FOR THE QUALITY ASSESSMENT OF A COMPONENT PRODUCED BY MEANS OF AN ADDITIVE MANUFACTURING METHOD

BACKGROUND OF THE INVENTION

The invention relates to a method for the quality assessment of a component produced by means of an additive manufacturing method.

Additive manufacturing methods refer to processes in which material is deposited layer by layer on the basis of digital 3D construction data in order to build up a component generatively by 3D printing. Additive manufacturing methods thus differ from conventional material-removing or primary shaping methods of fabrication. Instead of milling a work piece from a solid block, for example, additive manufacturing methods build up components layer by layer from one or a plurality of materials. Examples of additive manufacturing methods are generative laser sintering or laser melting methods, which, for example, are used for the manufacture of components for aircraft engines. Such a method is already known from DE 10 2004 017 769 B4, for example. In selective laser melting, thin layers of powder of the material or materials used are placed on a construction platform and locally melted and solidified by means of one or a plurality of laser beams. The construction platform is then lowered and another layer of powder is applied and again locally solidified. This cycle is repeated until the finished component is obtained. The finished component can then be further processed as needed or immediately used. In selective laser sintering, the component is produced in a similar way by laser-assisted sintering of powdered materials.

However, laser sintering and melting methods have not been used so far for serial production of components for aircraft engines. In addition, a process permit, a prerequisite of which is the monitoring of diverse process parameters, such as, for example, the laser power as well as the nature and state of the powdered material and the like, is required, in particular, for the use of components that are produced by generative laser methods and are subject to high stresses. In this case, the individual process parameters have to be monitored at intervals in the framework of a process monitoring by means of a respectively adapted, elaborate method of measurement. A method for monitoring layer buildup, which is known as such, is optical tomography, which affords an image for each component layer, the brightness values of which enable conclusions to be drawn about the quality of the additive fabrication process. The quantification of brightness values can be established on the basis of a number of influencing variables, but to date not on absolute values. A good target value process also is subject to different influences, such as, for instance, the component geometry, the loading of the construction platform, the position within the component, etc, and, as a result, can lead to various gray-scale value ranges, which, however, can still characterize a component that has fundamentally good quality.

SUMMARY OF THE INVENTION

The object of the present invention is to create a method by means of which an at least largely automated and quantifiable quality assessment of a component produced by means of an additive manufacturing method is made possible.

The object is achieved in accordance with the invention by a method having the features for the quality assessment of a component produced by means of an additive manufacturing method. Advantageous embodiments with appropriate enhancements of the invention are discussed in detail below.

A method by means of which an at least largely automated and quantifiable quality assessment of a component produced by means of an additive manufacturing method is made possible comprises, in accordance with the invention, at least the step a) preparation of a first data set, with the first data set comprising absolute limit values that each characterize a maximum allowed range of values at an assigned component position of the component being produced, b) acquisition of a second data set by means of an acquisition device, with the second data set comprising actual values corresponding to the first data set, which characterize the assigned component position of the component produced, and c) comparison of the first data set and the second data set by means of a computing device. In step c1), the component is then classified as being qualitatively fundamentally not OK if at least one actual value lies outside its assigned maximum allowed range of values. Alternatively, the component in step c2) is classified as being qualitatively fundamentally OK if no actual value lies outside its assigned maximum allowed range of values. If the component has been classified as being qualitatively fundamentally not OK, it can be concluded that there is a serious breakdown or malfunction. If the component has been classified as being qualitatively fundamentally OK, it can be assumed that the additive manufacturing method and the acquisition device fundamentally function. In this case, in a subsequent step d), a third data set is prepared, which comprises mean values that are determined from a plurality of actual values of the second data set by means of the computing device, wherein the plurality of actual values characterize an interrelated component region composed of a plurality of component positions. This leads to a corresponding reduction in data, because a plurality of measured actual values of a component region are compiled to obtain a mean value. Subsequently, in step e), at least one best-fit function that is dependent on the component geometry is determined on the basis of the third data set by means of the computing device. In other words, in step e), a best-fit function, that is, a smoothing function or approximation function, is determined by means of all mean values for the entire component. In this case, the kind of best-fit function fundamentally can be any suitable mathematical description that reproduces as accurately as possible the plot of the mean values through the component. In step f), threshold values that depend on the component geometry are then determined by means of the computing device, with the threshold values characterizing an allowed range of scatter of the actual values around the target values predetermined by the best-fit function. In other words, in step f), threshold values around this best-fit function are defined and thus characterize a targeting process or target values. The threshold values thus correspond to dynamic limit values that depend on the component geometry and delimit an allowed range of scatter of the individual component regions. In a following step g), it is checked by means of the computing device whether at least one actual value lies outside of the range of scatter characterized by the threshold values. If no actual value lies outside of the range of scatter, the component is classified in step g1) as being qualitatively OK. If at least one actual value lies outside the range of scatter, then, in step g2), all actual values that lie outside of the range of scatter are compiled to obtain a fifth data set, after which the component quality is assessed on the basis of the fifth data set and at least one predetermined quality criterion. In other words, it is examined first of all whether one or a plurality of actual values lies or lie outside the range of scatter characterized by a targeting process. If this is not the case, the component is in compliance with the desired standard and is classified as being qualitatively OK or as belonging to the highest quality class. In the other case, all actual values that deviate from the standard are isolated and stored in the fifth data set. In the further assessment, only this fifth data set is then still considered, as a result of which a further reduction in data is obtained. The assessment of the component quality on the basis of the fifth data set and at least one predetermined quality criterion can then lead to different outcomes. For example, the component can be classified as still being OK, but assigned to a lower quality class. Alternatively, however, the assessment may also reveal that, individually or in total, the deviations deviate from the target quality so seriously that the component is to be classified as being qualitatively not OK. A complete or at least a largely automated and quantified quality assessment and quality assurance of components that have been produced by an additive manufacturing method is thus made possible. In this case, it is to be emphasized that the person skilled in the art is aware that the sequence of different method steps can also be fundamentally altered. For example, steps a) and b) can be interchanged. It is also to be emphasized that the method can be applied not only to entire components, but also to only partially produced components or to individual component layers.

In an advantageous embodiment of the invention, an optical tomography device is used as the acquisition device. Preferably, in this case, the acquisition device affords gray-scale images with at least 16-bit depth. This makes possible a rapid and precise determination both of absolute limit values for the first data set and of actual values for the second data set.

Additional advantages ensue in that at least one absolute limit value of the first data set is predetermined on the basis of an empirical value and/or on the basis of a measured value of a reference component of flawless structure. In other words, the stipulation of the absolute limits occurs by way of empirical values and/or by way of test prototype jobs or cut sections thereof, which have been demonstrated to have formed a flawless and dense structure.

In another advantageous embodiment of the invention, it is provided that the additive manufacturing method and/or the acquisition device is checked or monitored if the component is classified in step c1) as being fundamentally not OK. If, in step c1), it has been established that the component is fundamentally not OK because at least one actual value lies outside of the permissible range defined by the absolute limit values, it is to be assumed that there is a serious flaw in the manufacturing method and/or in the acquisition device. A check of the additive manufacturing method can comprise, for example, the examining of a laser power, the material used, or other process parameter, such as, for example, the 3D data of the component. Alternatively or additionally, the proper functioning of the acquisition device is checked. In this way, fundamental malfunctions can be identified and eliminated, as a result of which a high component quality and a low reject are ensured.

In another advantageous embodiment of the invention, the mean values of the third data set are determined as an arithmetic mean and/or as a modus and/or as a median and/or as a geometric mean and/or as a harmonic mean and/or as a quadratic mean and/or as a cubic mean. In this way, one obtains for each component region a data point that describes the position of the actual value in relation to the component region being considered. Depending on the component or component region being considered, it is possible to determine the mean values by different computing procedures, as a result of which different contexts can optimally be taken into consideration in order to characterize the respective distribution of the actual values being considered.

Additional advantages ensue when the mean values of the third data set are determined on the basis of actual values, which characterize an irradiated layer area of the component and/or a region of an irradiated layer area of the component. In other words, the individual component layers or subregions thereof formed during the additive manufacturing method are used as the component region. In this way, mean values that each characterize a component layer are obtained. This makes possible an especially simple and rapid quality assessment of the entire component as well as of the individual component layers, so that, when deviations are determined in a certain layer, a corresponding rapid and simple adjustment of the additive manufacturing method is made possible.

Additional advantages ensue when the actual values in the fifth data set are initially weighted on the basis of at least one weighting factor for assessment of the component quality. This permits an improved quality assessment, because, as a result thereof, more important or more reliable actual values have a greater influence on the quality assessment than less important or unreliable actual values.

In another advantageous embodiment of the invention, it is provided that an indicator index and/or a number of indicators in the component and/or a distance from an adjacent indicator and/or a position in the component are or is used as a weighting factor. In this way, an improved weighting of flaws is made possible. In this case, the indicator index fundamentally describes a type of specific process deviation, which has a specific effect on the component. In accordance therewith, it has been shown to be advantageous when various indicator indices are used for different process deviations. The distance between adjacent indicators can be employed as a measure of the severity of an assigned process deviation or of an assigned flaw. Alternatively or additionally, the position of a process deviation or of a flaw within the component can be employed for assessment of the corresponding flaw. In this case, rear regions in the component are usually to be more strongly weighted than front regions.

In another embodiment of the invention, it has been shown to be advantageous when, as the quality criterion, a color value and/or a gray-scale value and/or a size and/or a shape is used. For example, various values from the image processing can be used for the formation of the indicator index in order to identify the kind or type and the severity of the respectively existing process deviation.

BRIEF DESCRIPTION OF THE DRAWING FIGURES

Figure 2:
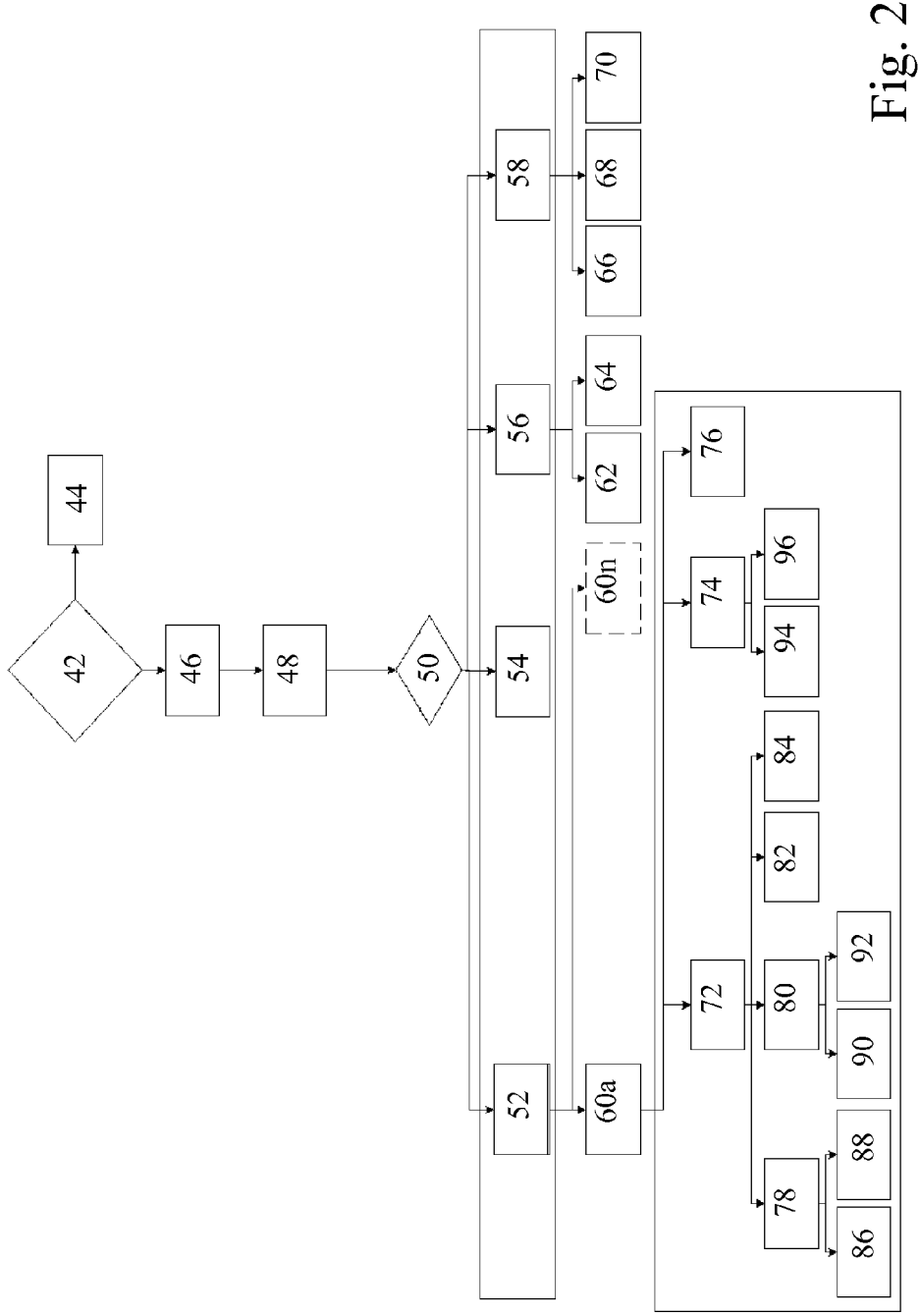

Additional features of the invention ensue from the claims and the exemplary embodiment as well as on the basis of the drawings. The features and combinations of features mentioned above in the description as well as the features and combinations of features mentioned below in the exemplary embodiment can be used not only in the combination respectively presented, but also in other combinations, without departing from the scope of the invention. Shown are:

FIG. 1 a flow chart, which shows the acquisition of layer data of a generatively produced component; and FIG. 2 a flow chart, which shows the quality assessment of the component produced.

DETAILED DESCRIPTION OF THE INVENTION

FIG. 1 shows a flow chart, which highlights in detail an exemplary embodiment of an acquisition of layer data of a generatively produced component. The method can fundamentally be carried out completely on a computer basis. The component can be a component for an aircraft engine and/or a turbomachine.

In a first step 10, an additive manufacturing of the component by means of a laser sintering and melting method, for example, is started. In this case, the component is formed in a known way iteratively from a plurality of layers on the basis of predetermined 3D design data. In step 12, a 16-bit gray-scale image is recorded for each layer n by means of an acquisition device (not shown) designed as an optical tomograph (OT), in which each pixel of the gray-scale image encodes a brightness value (actual value) at a component position of the component to be produced. All gray-scale images are compiled to obtain a second data set containing actual values. In step 14, the maximum gray-scale value and the sum of the gray-scale values over all pixels of the gray-scale image are determined for each gray-scale image. In step 16, it is checked whether the determined actual values lie partially or completely outside a maximum allowed value range, which is predetermined by a first data set containing absolute limit values for the component to be produced. The absolute limit values define a plausible range in which the targeting process should lie for each component. The definition of the absolute values occurs by way of empirical values or by way of test prototype jobs and cut sections thereof, which have been shown to have formed a flawless and dense structure. These absolute limit values serve primarily in order to reliably rule out a massive change of the laser power or other effects, such as wrongly chosen structural parameters or the like. It is also possible in this way to detect gross malfunctions of the OT system and, if applicable, to eliminate them. Therefore, the actual values are compared to their corresponding absolute value limits. In the present example, the absolute values limits are also encoded as gray-scale values, that is, as brightness values.

In step 18, a fundamentally optional documentation can occur. For example, the acquired layer images, the location, and/or the number of determined exceedings of absolute limit values for a specific component layer, the number of cumulative flaws up to the current point in time, and the like can be stored in a database by means of a computer and/or displayed by means of a display device.

Depending on the checking result in step 16, it is differentiated in step 20 whether the component or the currently checked component layer is fundamentally OK or fundamentally not OK. If a deviation from the absolute limit values has been found, it is evident that a serious process malfunction and/or a malfunction of the OT system have/has occurred. In this case, the manufacturing method and/or the acquisition device need to be examined and steps 12 to 16 need to be carried out once again.

In another case, this means that, if the currently checked component layer is fundamentally OK, serious malfunctions in the beam melting unit or in the measurement system can be ruled out. In accordance therewith, at least the above-described method steps 12 and 14 are repeated in steps 22 and 24, respectively, with the next respective component layer n+1 up to the end of the additive manufacturing method 26.

In step 28, all actual values or gray-scale values are compiled to obtain a second data set and compared to a first data set 32 in step 30 in order to check whether any of the determined actual values have impermissibly exceeded predetermined absolute values for the entire component. If the component is flawless, the layer data of the component in step 34 can be used for the definition of the first data set or for the definition of the targeting process. For this purpose, the mode and/or the arithmetic mean is determined for each component layer n (step 36). Furthermore, the mean value of all actual values is determined (step 38). Finally, the plot of the scatter, which depends on the component position, is determined for the component (step 40).

FIG. 2 shows a flow chart with the steps that are carried out for quality assessment of the produced component. In step 42, it is checked first of all whether the determined actual values of the second data set lie within the allowed absolute limits defined by the first data set. In an alternative step 42, it could also fundamentally be checked whether the mean values of the component layers each lie within corresponding absolute limit mean values. If a gross flaw, that is, an exceeding of the predetermined limit values exists, then the method is initially discontinued in step 44 in order to examine the fundamental functioning of the additive manufacturing method and/or of the acquisition device (OT system).

If it is ascertained that the manufacturing method and the OT system fundamentally function, then, in step 46, all gray-scale values of the construction job are prepared and the mean value or mode of all gray-scale values is determined from each layer. In this way, a data point is obtained for each component layer. On the basis of these mean values, a best-fit function, which depends on the component geometry and describes the geometry-dependent gray-scale value plot, is determined. Depending on the geometry of the built-up components, different plots of the gray-scale values are obtained. The kind of best-fit function can therefore be a best-fit line in the simplest case; also conceivable, however, are also all other suitable best-fit functions, such as, for example, polynomials of the n-th degree or other mathematical descriptions, which reproduce as exactly as possible the plot of the construction job.

The targeting process will be characterized in detail by way of defined limits around this best-fit function. For this purpose, dynamic threshold values, which depend on the component geometry and define a normal range of scatter of the individual component layers as a function of the component geometry and construction height, are determined.

In step 48, all actual values are then examined as to whether they lie within the standard or target limits defined by the best-fit function and the threshold values. If they do, the component is classified as being qualitatively OK. Otherwise, all actual values that lie outside of the range of scatter are compiled in a fifth data set and assessed in detail in step 50. This assessment can be carried out on the basis of several quality criteria and weighting factors.

An indicator index 52, the number of indicators in the component 54, the distance from the next indicator 56, and the position in the component 58 are used initially as weighting factors for the indicator. Starting from the indicator index 52, various kinds of indicators 60a . . . 60n can be provided. Starting from the distance from the next indicator 56, it is possible to employ the characteristic shape in the X/Y plane of the component 62 and/or the characteristic shape in the buildup direction Z of the component 64 for quality assessment. Starting from the position in the component 58, it can be checked whether the deviation lies in the volume of the component 66 and/or at the edge of the component 68 and/or whether it passes completely through the component 70.

As quality-relevant influence factors, which can be displayed individually or in groups, it is further possible to employ the determined gray-scale values actual values 72 and/or the magnitude of the actual values 74 present in the fifth data set and/or the geometric shapes 76 characterized by the fifth data set. Starting from the determined gray-scale values 72, the following parameters can be displayed individually and in any combination:

the maximum and minimum values 78;
the mean value of an indicator 80;
the plot or gradient 82; and/or
the scatter 84.

On the basis of the maximum and minimum values 78, it is further possible to display the corresponding absolute values 86 and/or the relative position of the maximum and minimum values 78 in relation to the mode or mean value 88. Correspondingly, it is possible, starting from the mean value of an indicator 80, to display the corresponding absolute value 90 and/or the relative position of mean value and mode with respect to each other 92.

Starting from the magnitude of the actual values 74 present in the fifth data set, it is possible to display the following parameters individually and in any combination:

characteristic shape in the X/Y plane 92; and
characteristic shape in the buildup direction Z 94.

On the basis of the mentioned characterization and quantification, a quality class of the component is then determined. Examples of possible quality classes are "reject," "good part," "decision," or equivalent terminologies. The values and parameters employed for the quantification of the quality classes can be established or examined on the basis of empirical values, such as material data, POD data (probability of detection—probability of detection of features/properties), NTD/DT reliability data (reliability of methods for material testing, ratio of "correct data" to "flaw alarm"), or the like.

What is claimed is:

1. A method for the quality assessment or the quality class of a component for a machine produced by means of an additive manufacturing method, comprising:
  a) preparation of a first data set, wherein the first data set comprises absolute limit values that each characterize a maximum allowed range of values at an assigned component position of a machine component being produced;
  a1) providing an optical tomography device as an acquisition device;
  b) acquisition of a second data set by means of the acquisition device that captures images of the machine component being produced, wherein the second data set comprises actual values corresponding to the first data set, which characterize the assigned component position of the machine component being produced;
  c) comparison of the first data set and the second data set by means of a computing device and
  c1) classification of the machine component as being qualitatively fundamentally not OK if at least one actual value lies outside its assigned maximum allowed range of values; or
  c2) classification of the component as being qualitatively fundamentally OK if no actual value lies outside its assigned maximum allowed range of values; and
  if the machine component has been classified as being qualitatively fundamentally not OK, it can be concluded that there is a serious breakdown or malfunction;
  if the machine component has been classified as being qualitatively fundamentally OK:
  d) preparation of a third data set, which comprises mean values that are determined from a plurality of actual values of the second data set by means of the computing device, wherein the plurality of actual values characterize an interrelated machine component region composed of a plurality of component positions;
  e) determination of at least one best-fit function that is dependent on a geometry of the machine component on the basis of the third data set by means of the computing device;
  f) determination of threshold values that depend on the geometry of the machine component by means of the computing device, wherein the threshold values characterize an allowed range of scatter of the actual values around target values predetermined by the best-fit function;
  g) checking by means of the computing device whether at least one actual value lies outside of the range of scatter characterized by the threshold values, and
    g1) if no actual value lies outside of the range of scatter, the machine component is classified as being qualitatively OK; or
    g2) if at least one actual value lies outside the range of scatter, then all actual values that lie outside of the range of scatter are compiled to obtain a fifth data set, and a quality of the machine component is assessed on the basis of the fifth data set and at least one predetermined quality criterion.

2. The method according to claim 1, wherein at least one absolute limit value of the first data set is predetermined on the basis of an empirical value and/or on the basis of a measured value of a reference component of flawless structure.

3. The method according to claim 1, wherein the additive manufacturing method and/or the acquisition device is checked if the machine component is classified in step c1) as being fundamentally not OK.

4. The method according to claim 1, wherein the mean values of the third data set are determined as an arithmetic mean and/or as a mode and/or as a median and/or as a geometric mean and/or as a harmonic mean and/or as a quadratic mean and/or as a cubic mean.

5. The method according to claim 1, wherein the mean values of the third data set are determined on the basis of the actual values that characterize an irradiated layer area of the machine component and/or a region of an irradiated layer area of the machine component.

6. The method according to claim 1, the actual values in the fifth data set are weighted initially on the basis of at least one weighting factor for assessment of the quality of the machine component.

7. The method according to claim 6, wherein, as weighting factor, an indicator index and/or a number of indicators in the machine component and/or a distance from an adjacent indicator and/or a position in the machine component are or is used.

8. The method according to claim 1, wherein as quality criterion, a color value and/or a gray-scale value and/or a size and/or a shape is used.

\* \* \* \* \*